US 6,277,860 B1

(12) United States Patent
Sugie et al.

(10) Patent No.: US 6,277,860 B1
(45) Date of Patent: Aug. 21, 2001

(54) FUROPYRIDINE ANTIBACTERIALS

(75) Inventors: Yutaka Sugie; Akemi Sugiura; Nobuji Yoshikawa, all of Nagoya (JP); Susan J. I Truesdell, Warwick, RI (US); John W. Wong, East Lyme, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/430,763

(22) Filed: Oct. 29, 1999

(51) Int. Cl.$^7$ .................. A61K 31/436; A61K 31/4355; C07D 491/048; C07D 491/153; A61P 31/04

(52) U.S. Cl. .......................... 514/291; 514/302; 546/90; 546/92; 546/116

(58) Field of Search ................. 546/116, 90, 92; 574/302, 291; 435/118, 911, 254.1, 255.7

(56) References Cited

U.S. PATENT DOCUMENTS 3,535,322 * 10/1970 Georgiadis .
4,973,693 * 11/1990 Goto .

FOREIGN PATENT DOCUMENTS

196298825 * 1/1998 (DE) .
9743277 * 11/1997 (WO) .
6808173 * 6/1969 (ZA) .

OTHER PUBLICATIONS

Tezuka Y et al. Chem. Pharm. Bull. 42(12), pp. 2612–2617, 1994.*

* cited by examiner

*Primary Examiner*—Evelyn Mei Huang
(74) *Attorney, Agent, or Firm*—Peter C. Richardson; Paul H. Ginsburg; Jeffrey N. Myers

(57) ABSTRACT

This invention provides a compound of formula (I):

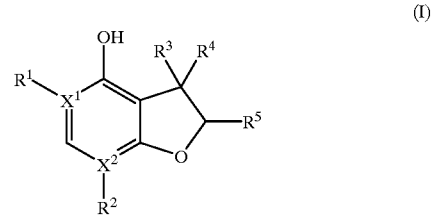

(I)

or pharmaceutically acceptable salts thereof, wherein $X^1$ and $X^2$ are C or N, respectively; $R^1$ and $R^2$ are independently phenyl optionally substituted with a hydroxy group with proviso that $X^1$ and $X^2$ are not simultaneously C or N, when $X^1$ is N, $R^1$ is absent, and when $X^2$ is N, $R^2$ is absent; $R^3$ is methyl or hydroxymethyl; $R^4$ is formyl, hydroxymethyl or hydroxy $C_{3-6}$ alkenyl; $R^5$ is hydroxy, $C_{3-6}$ alkenyl or hydroxy $C_{3-6}$ alkenyl; or $R^4$ and $R^5$, together with the carbon atoms in the furopyridine ring to which they are attached, may form the following ring (to be fused with the furopyridine ring):

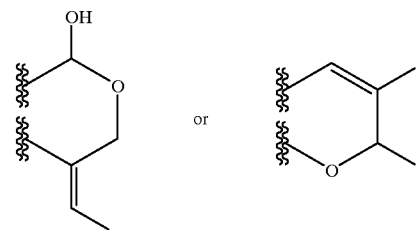

with the proviso that when $R^3$ is methyl and $R^5$ is 2-buten-2-yl, $X^2$ is not N. These compounds and pharmaceutical compositions containing such compounds are useful for treating infectious diseases caused by bacteria.

4 Claims, No Drawings

FUROPYRIDINE ANTIBACTERIALS

This application claims the benefit of priority from PCT International Application No. PCT/IB98/01748 filed Nov. 2, 1998.

TECHNICAL FIELD

This invention relates to furopyridine antibacterials, and particularly to furopyridine antibacterials produced by fermentation of a fungus *Cladobotryum varium* (FERM BP-5732) and to their biotransformation products by the microorganisms *Calonectria decora* (FERM BP-6124), *Cunninghamella echinulata* var. *elegans* (FERM BP-6126), or an unidentified bacterium (FERM BP-6125). This invention also relates to pharmaceutical compositions comprising the same, which are useful in the treatment of diseases, disorders and adverse conditions caused by infection by various bacteria, including multidrug resistant strains of Staphylococcus sp., Streptococcus sp. and Enterococcus sp.

BACKGROUND ART

People have received great health care benefit from many kinds of anti-infectives since penicillin was found (A. Fleming, 1929) and developed (H. W. Florey et. al., 1941). However, there has been an alarming increase, recently, in the incidence of multidrug resistant infections that is limiting the utility of many standard agents, such as β-lactams, macrolides and quinolones. For an example, methicillin-resistant *Staphylococcus aureus* (MRSA) and vancomycin-resistant Enterococcus species are now co-resistant to essentially all other antibiotic classes. Multidrug resistant *Streptococcus pneumoniae* is also one of the most important bacterial pathogens due to its frequency in upper and lower respiratory tract infections in both children and adults. *S. pneumoniae* is rapidly becoming resistant to all presently available therapies. Commonly prescribed anti-infectives such as β-lactams and the current macrolides are no longer reliably effective.

These multidrug resistant bacteria are not limited to hospitals but also occur in a variety of human communities world-wide. In many cases, multidrug resistant infections can lead to potentially fatal conditions and require hospitalization. The emergence of such multidrug resistant bacteria prompted drug discovery programs. For example, dipeptides are described as new antibiotics with potent antibacterial activity against MRSA (R. M. Williams et al., J. Antibiotics, 51(2), 189–201, 1998). To provide a compound having good activity against various bacteria, including multidrug resistant bacteria such as Staphylococcus sp., Streptococcus sp. and Enterococcus sp., is not only required by serious medical need, but by the overall health care cost savings achieved by minimizing treatment failures, laboratory testing, and hospitalization.

The object of the present invention is to provide furopyridine compounds which have good antibacterial activity against various bacteria, including multidrug resistant bacteria, and to provide a pharmaceutical composition comprising the same. A variety of furopyridine compounds are known. For example, in German patent publication DE 4218978 A1, furopyridine compounds are disclosed as liquid crystal materials. Also, International Publication Number WO 97/11076 discloses furopyridine compounds as fungicides.

Another object of the present invention is to provide processes for producing the furopyridine compounds.

BRIEF DISCLOSURE OF THE INVENTION

The present invention provides a furopyridine compound of formula (I):

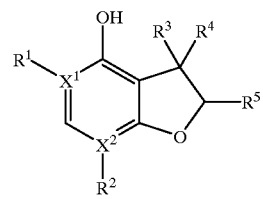

(I)

or pharmaceutically acceptable salts thereof, wherein
$X^1$ and $X^2$ are C or N;
$R^1$ and $R^2$ are independently phenyl optionally substituted with a hydroxy group with proviso that $X^1$ and $X^2$ are not simultaneously C or N; when $X^1$ is N, $R^1$ is absent; and when $X^2$ is N, $R^2$ is absent;
$R^3$ is methyl or hydroxymethyl;
$R^4$ is formyl, hydroxymethyl or hydroxy $C_{3-6}$ alkenyl; and
$R^5$ is hydroxy, $C_{3-6}$ alkenyl or hydroxy $C_{3-6}$ alkenyl; or
$R^4$ and $R^5$, together with the carbon atoms in the furopyridine ring to which they are attached, may form the following ring (to be fused with the furopyridine ring):

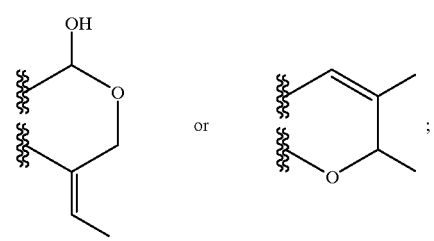

with the proviso that when $R^3$ is methyl and $R^5$ is 2-buten-2-yl, $X^2$ is not N.

This invention also provides a compound having the following characteristics:
1) a molecular formula $C_{19}H_{19}NO_2$;
2) absorption maxima in methanol in the ultraviolet light region of the spectrum at 206.0 and 247.0 nm;
3) an optical rotation of $[\alpha]_D^{24}=+13.3°$ at a concentration of 6% in methanol;
4) characteristic absorption in the infrared region, when pelleted in KBr, at the following wavelengths ($cm^{-1}$): 3378, 2963, 1647, 1614, 1450, 1427, 1228, 1042, 823, 774 and 694;
5) $^1H$ NMR spectrum (270 MHz) having major peaks at δ 7.52 (m, 2H), 7.47 (s, 1H), 7.31 (m, 2H), 7.24 (m, I H), 5.36 (brs, 1H), 3.13 (brs, 1H), 2.78 (q, J=7.3 Hz, 1H), 1.67 (s, 3H), 1.58 (s, 3H), 1.18 (d, J=7.3 Hz, 3H); and
6) $^{13}C$ NMR spectrum (67.5 MHz) having major peaks at δ 165.03 (s), 162.55 (s), 151.38 (s), 135.38 (d), 130.23 (s), 129.71 (d×2), 128.79 (d×2), 128.15 (d), 127.81 (d), 114.34 (s), 111.06 (s), 104.28 (s), 58.32 (d), 50.30 (d), 26.97 (q), 20.93 (q), 15.28 (q);
or pharmaceutically acceptable salts thereof.

The furopyridine compounds of the present invention exhibit antibiotic activities against bacteria including multidrug resistant strains of Staphylococcus sp., Streptococcus sp. and Enterococcus sp. Therefore, the present invention also provides a pharmaceutical composition for use in the treatment of infectious diseases caused by bacteria, which comprises a compound of formula (I) or a pharmaceutically acceptable salt thereof in an amount effective in such treatments; and a pharmaceutically acceptable carrier.

Also, the present invention is directed to a method of treating infectious diseases caused by bacteria, in a mammalian subject, which comprises administering to said subject a therapeutically effective amount of a compound of formula (I).

DETAILED DISCLOSURE OF THE INVENTION

As used herein, the term "multidrug resistant" means a microorganism that is resistant to such antibiotics as macrolides and β-lactams. The antibiotics include penicillin, erythromycin, methicillin and vancomycin.

This invention includes any possible stereoisomers and tautomers of compounds of the formula (I).

More specific compounds of this invention are those of formula (I), wherein $X^1$ is C, $X^2$ is N, $R^1$ is phenyl, $R^2$ is absent, $R^3$ is methyl, $R^4$ and $R^5$ together form the following ring to be fused with furopyridine ring:

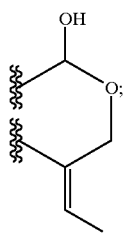

$X^1$ is C, $X^2$ is N, $R^1$ is phenyl, $R^2$ is absent, $R^3$ and $R^4$ are hydroxymethyl, and $R^5$ is 2-buten-2-yl;

$X^1$ is C, $X^2$ is N, $R^1$ is phenyl, $R^2$ is absent, $R^3$ is methyl, $R^4$ is formyl, and $R^5$ is 4-hydroxy-2-buten-2-yl;

$X^1$ is C, $X^2$ is N, $R^1$ is phenyl, $R^2$ is absent, $R^3$ is methyl, $R^4$ is hydroxymethyl, and $R^5$ is 4-hydroxy-2-buten-2-yl;

$X^1$ is N; $X^2$ is C; $R^1$ is absent; $R^2$ is phenyl; $R^3$ is methyl; $R^4$ is hydroxymethyl; and $R^5$ is 2-buten-2-yl;

$X^1$ is N; $X^2$ is C; $R^1$ is absent; $R^2$ is phenyl; $R^3$ is methyl; $R^4$ and $R^5$, together with the carbon atoms to which they are attached, form the following ring to be fused with furopyridine ring:

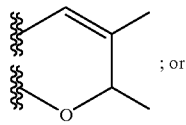

$X^1$ is N; $X^2$ is C; $R^1$ is absent; $R^2$ is phenyl; $R^3$ is methyl; $R^4$ is 3-hydroxy-2-methyl-1-buten-1-yl; and $R^5$ is OH.

Specific individual compounds of this invention are selected from

2R*,3R*-2,3-dihydro-2-[(E)-2-buten-2-yl]-4-hydroxy-3-hydroxymethyl-3-methyl-7-phenylfuro[3,2-c]pyridine or its salts;

2R*,4aR*,9aS*-4a,9a-dihydro-5-hydroxy-8-phenyl-2,3,4a-trimethyl-2H-pyrano[2,3-b]furo[3,2-c]pyridine or its salts;

1R*,4bS*-1,3,4a,4b-tetrahydro-9-hydroxy-4b-methyl-8-phenyl-4-(E)-ethylidenepyrano[4,3-b]furo[2,3-b]pyridine or its salts;

2,3-dihydro-2-[(E)-2-buten-2-yl]-3,3-di-(hydroxymethyl)-4-hydroxy-5-phenylfuro[2,3-b]pyridine or its salts;

2R*,3S*-2,3-dihydro-2,4-dihydroxy-3-[(E)-3-hydroxy-2-methyl-1-butenyl]-7-phenylfuro[3,2-c]pyridine or its salts;

2R*,3R*-2,3-dihydro-4-hydroxy-2-[(E)-4-hydroxy-2-buten-2-yl]-3-methyl-5-phenylfuro[2,3-b]pyridine-3-carbaldehyde or its salts;

2R*,3S*-2,3-dihydro-4-hydroxy-2-[(E)-4-hydroxy-2-buten-2-yl]-3-hydroxymethyl-3-methyl-5-phenylfuro[2,3-b]pyridine or its salts.

The most preferred individual compound to be contained in the pharmaceutical composition is 2R*,3R*-2,3-dihydro-2-[(E)-2-buten-2-yl]-4-hydroxy-3-methyl-5-phenylfuro[2,3-b]pyridine-3-carbaldehyde. This compound (hereinafter referred to as Compound 1) is believed to have the following structure:

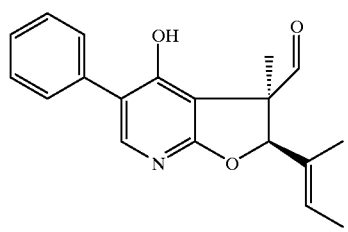

The microorganisms used in this invention include a strain of *Cladobotryum varium* which was purchased from the New York Botanical Garden (The Bronx, New York N.Y., 10458, U.S.A.). It was deposited under the accession number FERM BP-5732 to National Institute of Bioscience and Human-Technology, Agency of Industrial Science and Technology (located at 1-3,Higashi 1-chome, Tsukuba, Ibaraki 305, Japan) under the Budapest treaty on Oct. 29, 1996. The taxonomical properties of *Cladobotryum varium* are found in Gams, K. W. and Hoozemans, A. C. M., *Persoonia* 6, 96–110,1970.

The other microorganisms used in this invention are a strain of *Calonectria decora* (FERM BP-6124), *Cunninghamella echinulata* var. *elegans* (FERM BP-6126) and an Unidentified bacterium (FERM BP-6125) which were purchased from the American Type Culture Collection (10801 University Blvd. Manassas, Va. 20110-2209 USA). These were deposited under the above-shown accession numbers to National Institute of Bioscience and Human-Technology, Agency of Industrial Science and Technology (located at 1-3,Higashi 1-chome, Tsukuba, Ibaraki 305, Japan) under the Budapest treaty on Sep. 26, 1997.

According to the present invention, aerobic fermentation of FERM BP-5732, or a mutant or recombinant form thereof may yield the furopyridine compounds of formula (I) wherein $X^1$ is C, $X^2$ is N, $R^1$ is phenyl, $R^2$ is absent, $R^3$ is methyl, $R^4$ is formyl, and $R^5$ is 2-buten-2-yl;

$X^1$ is C, $X^2$ is N, $R^1$ is phenyl, $R^2$ is absent, $R^3$ is methyl, $R^4$ is hydroxymethyl, and $R^5$ is 2-buten-2-yl;

$X^1$ is C, $X^2$ is N, $R^1$ is phenyl, $R^2$ is absent, $R^3$ is methyl, $R^4$ and $R^5$ together form the following ring to be fused with furopyridine ring:

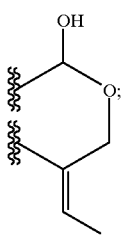

$X^1$ is C, $X^2$ is N, $R^1$ is phenyl, $R^2$ is absent, $R^3$ and $R^4$ are hydroxymethyl, and $R^5$ is 2-buten-2-yl;

$X^1$ is N; $X^2$ is C; $R^1$ is absent; $R^2$ is phenyl; $R^3$ is methyl; $R^4$ is hydroxymethyl; and $R^5$ is 2-buten-2-yl;

$X^1$ is N; $X^2$ is C; $R^1$ is absent; $R^2$ is phenyl; $R^3$ is methyl; $R^4$ and $R^5$, together with the carbon atoms to which they are attached, form the following ring to be fused with furopyridine ring:

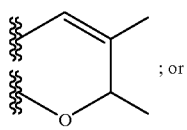

$X^1$ is N; $X^2$ is C; $R^1$ is absent; $R^2$ is phenyl; $R^3$ is methyl; $R^4$ is 3-hydroxy-2-methyl-i -buten-1-yl; and $R^5$ is OH.

Aerobic fermentation of FERM BP-5732 may also yield the compound having the following characteristics:

1) a molecular formula $C_{19}H_{19}NO_2$;
2) absorption maxima in methanol in the ultraviolet light region of the spectrum at 206.0 and 247.0 nm;
3) an optical rotation of $[\alpha]_D^{24} = +13.3°$ at a concentration of 6% in methanol;
4) characteristic absorption in the infrared region, when pelleted in KBr, at the following wavelengths ($cm^{-1}$): 3378, 2963, 1647, 1614, 1450, 1427, 1228, 1042, 823, 774 and 694;
5) $^1H$ NMR spectrum (270 MHz) having major peaks at δ 7.52 (m, 2H), 7.47 (s, 1H), 7.31 (m, 2H), 7.24 (m, 1H), 5.36 (brs, 1H), 3.13 (brs, 1H), 2.78 (q, J=7.3 Hz, 1H), 1.67 (s, 3H), 1.58 (s, 3H), 1.18 (d,J=7.3 Hz, 3H); and
6) $^{13}C$ NMR spectrum (270 MHz) having major peaks at δ 165.03 (s), 162.55 (s), 151.38 (s), 135.38 (d), 130.23 (s), 129.71 (d×2), 128.79 (d×2), 128.15 (d), 127.81 (d), 114.34 (s), 111.06 (s), 104.28 (s), 58.32 (d), 50.30 (d), 26.97 (q), 20.93 (q), 15.28 (q). This compound is hereinafter referred to as Compound 2.

The production of these compounds can be achieved by the fermentation of FERM BP-5732 at a temperature of 15 to 50° C., preferably 25 to 35° C. for 3 to 30 days, preferably 7 to 20 days in an aqueous nutrient medium or on a solid support in an aqueous nutrient medium. The pH of medium may be adjusted in the range from 4.0 to 9.0, preferably from 5. 0 to 7.0. Cultivation of FERM BP-5732 to produce said furopyridine compounds usually takes place at a temperature of 20 to 35° C. for 7 to 21 days. The pH of medium may be adjusted in the range from 4.0 to 9.0, preferably from 5.0 to 7.0.

Nutrient media useful for the fermentation include a source of assimilable carbon such as sugars, starches and glycerol; and a source of organic nitrogen such as casein, enzymatic digest of casein, soybean meal, cotton seed meal, peanut meal, wheat gluten, soy flour, meat extract and fish meal. A source of growth substances such as mineral salts, sodium chloride and calcium carbonate; and trace elements such as iron, magnesium, copper, zinc, cobalt and manganese may also be utilized with advantageous results.

The amount of the insoluble material for surface cultures may range 10 to 50% (w/v). Suitable insoluble materials useful for fermentation include sands, cracked stones, wood chips and whole and broken grains, such as buckwheat, oatmeal, cracked corn, millet, etc.

Aeration of the medium in fermentors for submerged growth is maintained at 3 to 200%, preferably at 50 to 150% volumes of sterile air per volume of the medium per minute. The rate of agitation depends on the type of the agitator employed. A shake flask is usually run at 150 to 250 rpm whereas a fermentor is usually run at 300 to 2,000 rpm. Aseptic conditions must, of course, be maintained through the transfer of the organism and throughout its growth. If excessive foaming is encountered during submerged fermentation in aqueous media, antifoam agents such as polypropylene glycols or silicones may be added to the fermentation medium.

Strains of *Calonectria decora* (FERM BP-6124), *Cunninghamella echinulata* var. *elegans* (FERM BP-6126), and an unidentified bacterium (FERM BP-6125), can be used to biotransform Compound 1 (2R*,3R*-2,3-dihydro-2-[(E)-2-buten-2-yl]-4-hydroxy-3-methyl-5-phenylfuro[2,3-b]pyridine-3-carbaldehyde). These microorganisms were deposited, with the accession number shown after the name of each microorganism, to National Institute of Bioscience and Human-Technology, Agency of Industrial Science and Technology (located at 1-3,Higashi 1-chome, Tsukuba, Ibaraki 305, Japan) under the Budapest treaty on Sep. 26, 1997.

In this invention, other strains belonging to genera such as Calonectria and Cunninghamella and other microorganisms which are capable of above biotransformation can be also used. The mutant or recombinant form of the above strains, having the ability to biotransform Compound 1 can be used. Such mutant or recombinant may be obtained by spontaneous mutation, artificial mutation with ultraviolet radiation, or treatment with mutagen such as N-methyl-N'-nitro-N-nitrosoguanidine or ethyl methanesulfonate, or a cell technology method such as cell fusion, gene manipulation or the like, according to well-known methods.

According to the present invention, the biotransformation of Compound 1 may be achieved by aerobic fermentation of FERM BP-6124, FERM BP-6125, FERM BP-6126, or a mutant or recombinant form thereof with the furopyridine Compound 1, under conditions similar to those generally employed to produce bioactive compounds by biotransformation.

Briefly, FERM BP-6124, FERM BP-6125, FERM BP-6126, or a mutant or recombinant form thereof, is fermented with the furopyridine Compound 1 in aqueous nutrient media or on the surface of insoluble materials suspended in an aqueous nutrient medium. Nutrient media and fermentation conditions useful for the biotransformation are basically the same as described above for the fermentation of FERM BP-5732. The furopyridine Compound 1 can be added into the medium prior to the fermentation, or can be added to the fermentation broth preferably 1 to 2 days after starting the cultivation, either in suspension or solution forms. To make suspension or solution of the furopyridine Compound 1, any materials used for the cultivation media and small amount of organic solvents such as dimethylsulfoxide or ethanol can be used. Cultivation of FERM BP-6124, FERM BP-6125 or FERM BP-6126 to biotransform the furopyridine Compound 1 takes place at a temperature of 15 to 50° C., preferably 25 to 35° C. for 3 to 30 days, preferably 7 to 20 days. The pH of medium may be adjusted in the range from 4.0 to 9.0, preferably from 5.0 to 7.0.

The furopyridine compounds of this invention may be isolated by standard techniques such as extraction and various chromatographic techniques. The furopyridine compounds shown in Examples were isolated in a substantially pure form from the fermentation mixtures, and identified by various spectroscopic techniques such as UV spectrophotometry, NMR and mass spectrometries. According to the analysis, the furopyridine compounds prepared by fermentation of FERM BP-5732 are believed to be the following:

2R*,3R*-2,3-dihydro-2-[(E)-2-buten-2-yl]-4-hydroxy-3-methyl-5-phenylfuro[2,3-b]pyridine-3-carbaldehyde or its salts;

2R*,3S*-2,3-dihydro-2-[(E)-2-buten-2-yl]-4-hydroxy-3-hydroxymethyl-3-methyl-5-phenylfuro[2,3-b]pyridine or its salts;

2R*,3R*-2,3-dihydro-2-[(E)-2-buten-2-yl]-4-hydroxy-3-hydroxymethyl-3-methyl-7-phenylfuro[3,2-c]pyridine or its salts;

2R*,4aR*,9aS*-4a,9a-dihydro-5-hydroxy-8-phenyl-2,3,4a-trimethyl-2H-pyrano[2,3-b]furo[3,2-c]pyridine or its salts;

1 R*,4bS*-1,3,4a,4b-tetrahydro-9-hydroxy-4b-methyl-8-phenyl-4-(E)-ethylidenepyrano[4,3-b]furo[2,3-b]pyridine or its salts;

2,3-dihydro-2-[(E)-2-buten-2-yl] -3,3-di-(hydroxymethyl)-4-hydroxy-5-phenylfuro[2,3-b]pyridine or its salts;

2R*,3S*-2,3-dihydro-2,4-dihydroxy-3-[(E)-3-hydroxy-2-methyl-1-butenyl]-7-phenylfuro[3,2-c]pyridine or its salts.

The compound, 2R*,3S*-2,3-dihydro-2,4-dihydroxy-3-[(E)-3-hydroxy-2-methyl-1-butenyl]-7-phenylfuro[3,2-c]pyridine is composed of two diastereomers. These diastereomers are, herein after, referred to as diastereomer A and diastereomer B, respectively.

The culture of FERM BP-6124, FERM BP-6125, and FERM BP-6126 may yield three different compounds on incubation with Compound 1. The compounds isolated from cultures FERM BP-6124, FERM BP-6125, and FERM BP-6126 are believed to be:

2R*,3R*-2,3-dihydro-4-hydroxy-2-[(E)-4-hydroxy-2-buten-2-yl]-3-methyl-5-phenylfuro[2,3-b]pyridine-3-carbaldehyde;

2R*,3S*-2,3-dihydro-4-hydroxy-2-[(E)-4-hydroxy-2-buten-2-yl]-3-hydroxymethyl-3-methyl-5-phenylfuro[2,3-b]pyridine; and 2R*,3R*-2,3-dihydro-2-[(E)-2-buten-2-yl]-4-hydroxy-5-(4-hydroxyphenyl)-3-methylfuro[2,3-b]pyridine-3-carbaldehyde, respectively.

Although we could not reveal the structure of Compound 2 contained in the broth obtained by fermentation of FERM BP-5732 due to the small amount of the compound available for the analysis, it is believed to have a novel chemical formula related to the above-identified furopyridine compounds of this invention whose structures were revealed.

Administration

The furopyridine compounds of the present invention are useful in the treatment of diseases, disorders and adverse conditions caused by infection by various bacteria, including multidrug resistant strains of Staphylococcus sp., Streptococcus sp. and Enterococcus sp. For use as an anti-infective agent in a mammalian subject, especially a human subject, the furopyridine compounds of the present invention can be administered either alone, as their pharmaceutically-acceptable salts, with other antibiotics or with an inert carrier in a pharmaceutical composition, according to standard pharmaceutical practice. The compounds can be given by parenteral or oral administration. The active ingredient may be compounded, for example, with the usual non-toxic, pharmaceutically acceptable carriers for tablets, pellets, capsules, suppositories, solutions, emulsions, suspensions and other forms suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations. In addition, if needed, auxiliary, stabilizing and coloring agents and perfumes may be used. In general, the furopyridine compounds of this invention are present in such dosage forms at concentration levels ranging 5 to 70% by weight, preferably 10 to 50% by weight.

The furopyridine compounds of this invention can be used in mammalian subjects as anti-infective agents in dosages ranging from 0.01 to 100 mg/kg. The dosage to be used in a particular case will vary according to a number of factors such as the disease state or condition being treated, the potency of the individual compound being administered, the response of the particular subject and the route of administration. However, when one of the furopyridine compounds of this invention is used in a human patient to treat diseases, disorders and adverse conditions caused by the infection of various bacteria, the usual oral or parenteral dosage will be in the range from 0.5 to 250 mg and preferably 5 to 250 mg, one to four times per day.

Antibacterial Assay

Antibacterial activity can be evaluated by a serial agar dilution method which determines a minimum inhibitory concentration (MIC) of each furopyridine compound, as shown below.

1. Microorganisms

Drug resistant strains used in the assay are summarized in the following table. Other strains which have similar characteristics of resistance to drugs may be also used. Such strains are usually available for those skilled in the art.

TABLE

Multidrug resistant strains used in the assay

| Species | Antibiotics used | MIC | Source |
|---|---|---|---|
| Enterococcus faecalis 03A1069 | penicillin G | 6 µg/ml | CDC/Missouri |
| | azithromycin | >256 µg/ml | Original |
| | vancomycin | 24 µg/ml | ID = HIP2025 |
| | cephalothin | 128 µg/ml | |
| | chloramphenicol | 16 µg/ml | |
| Staphylococcus aureus 01A1105 | penicillin G | 64 µg/ml | San Francisco |
| | methicillin | >256 µg/ml | General Hospital |
| | erythromycin | >256 µg/ml | Original |
| | clindamycin | >256 µg/ml | ID = M494683 |
| | tetracycline | 128 µg/ml | |
| | cefataxime | >256 µg/ml | |
| | gentamicin | 64 µg/ml | |
| | ciprofloxacin | >32 µg/ml | |
| Storeptococcus pyogenes | erythromycin | >64 µg/ml | SCICOR |
| | clindamycin | >64 µg/ml | |

TABLE-continued

Multidrug resistant strains used in the assay

| Species | Antibiotics used | MIC | Source |
|---|---|---|---|
| 02C1068 | azithromycin | >16 µg/ml | |
| | streptomycin | — | |
| | kanamycin | — | |
| Escherichia coli 51A0266 | vancomycin | >128 µg/ml | Clinical sample from urine; New London CT |

MIC: minimum inhibitory concentration; for more detail see below.

2. Preparation of Stock Cultures

Each strain of S. aureus 01A1105, E faecalis 03A1069 and E. coli 51A0266 is inoculated and grown in tube containing 10 ml of Trypticase Soy Broth (TSB, DIFCO), overnight at 37° C. shaking at 200 rpm. The cell-concentration of the culture is adjusted by dilution with TSB and 50% aqueous glycerol to an optical density of 1.4 at 600 nm (light path=1 cm) and a final glycerol concentration of 20%. The diluted culture is dispensed to cryotubes, 1 ml per vial, and stored at −80° C. until its use.

The strain of S. pyogenes 02C1068 was inoculated and grown in tubes, containing 10 ml of TSB with 0.5 ml of lysed horse blood (Nippon Bio-Supply Center), statically for 24 hours at 37° C. After the incubation, the cells were centrifuged and resuspended in a mixture of 50% aqueous glycerol (4 ml) and defibrinated sheep blood (6 ml, Nippon Bio-Supply Center). The resulting cell-suspension was dispensed to cryotubes, 1 ml per vial, and stored at −80° C. until its use.

3. Preparation of Assay Plates

Each stock culture, 200 µl for S. aureus and E. coli and 1 ml for E. faecalis, is added to 100 ml of Mueller Hinton medium (DIFCO), mixed and poured into an assay plate. The stock culture (1 ml) of S. pyogenes is inoculated into a tube containing 20 ml TSB and 1.0 ml defibrinated horse blood (Nippon Bio-Supply Center), and incubated statically at 37° C. for 24 hours. The incubated culture (5 ml) and 5 ml of sheep blood (Nippon Bio-Supply Center) were added to Mueller Hinton medium (100 ml), mixed and poured into an assay plate.

4. Detection of Antibacterial Activity

Sample solution is loaded and dried on a paper disk (i.d. 6 mm, thin, Advantec) which is placed on the assay plate and incubated overnight at 37° C. The activity is determined by measuring the size of growth-inhibition zone around the disk. As controls, vancomycin 1 µg and tetracycline 1 µg disks are used.

For determination of minimum inhibitory concentration (MIC), serial agar dilution method is used with same incubation condition as described above. The growth of bacteria is monitored by measuring the optical density at 655 nm.

EXAMPLES

The present invention is illustrated by the following examples. However, it should be understood that the invention is not limited to the specific details of these examples.

Example 1

Furopyridine Compounds Produced By the Fermentation of Cladobotryum varium, FERM BP-5732

Fermentation of Cladobotryum varium, FERM BP-5732

(A) One hundred mL of Medium-1 (potato dextrose broth 2.4%, yeast extract 0.5% and agar 0.1%/o) in two 500-mL flasks was inoculated with a vegetative cell suspension from a slant culture of FERM BP-5732. The flasks were shaken at 26° C. for 4 days on a rotary shaker with 7-cm throw at 210 rpm, to obtain seed cultures. The seed cultures in the 2 flasks were used to inoculate 5 mL each into thirty 500-mL flasks containing 100 mL of Medium-2 (glucose 1%, glycerol 6.6%, NZ Amine Type A 0.5%, ammonium sulfate 0.2%, defatted soybean meal 0.5%, tomato paste 0.5%, sodium citrate 0.2% and pH 7.0) and 30 g buckwheat. Incubation was carried out at 26° C. for 14 to 21 days.

(B) One hundred mL of Medium-1 (potato dextrose broth 2.4%, yeast extract 0.5% and agar 0.1%) in a 500-mL flask was inoculated with a vegetative cell suspension from a slant culture of FERM BP-5732. The flask was shaken at 26° C. for 4 days on a rotary shaker with 7-cm throw at 210 rpm, to obtain a first seed culture. A 500-mL flask containing Medium-1 (150 mL) was inoculated with 5 mL of the first seed culture. The flask was shaken at 26° C. for 3 days on a rotary shaker, to obtain a second seed culture. The second seed culture was used to inoculate a 6-L fermentation vessel containing 3 L of sterile medium (Medium-3: glycerol 8.5%, soybean meal 0.5%, corn flour 1.0% and corn steep liquor powder 0.25% and pH 5.0). The broth was fermented at 26° C. for 12 days with stirring at 1,700 rpm and aeration at 3 L per min.

Extraction and Isolation

The fermentation broth (3 L) was extracted with 3 L of ethanol and filtered. The filtrate was concentrated to aqueous solution (500 mL) and was applied onto a Diaion HP20 (Mitsubishikasei) column and eluted with 30%, 50% and 100% aqueous methanol and acetone. The methanol and acetone fractions were mixed, evaporated to dryness, reconstituted with 50% aqueous methanol, then loaded onto an ODS column and eluted with 70% aqueous methanol. The active fraction (3.1 g) was applied onto Sephadex LH-20 column (160 mL, methanol). Fractions showing activity were pooled, and evaporated material (1.7 g) was further separated by multiple injections on HPLC: YMC-pack ODS AM SH-343-5AM column (20×250 mm, sold under the tradename of Yamamura), eluting with methanol-water (13:7) for 40 min. at a flow rate of 10 mL/min. Detection was by UV absorbance at 240 nm. The eluted peak was collected to yield the following compounds:

2R*,3R*-2,3-dihydro-2-[(E)-2-buten-2-yl]-4-hydroxy-3-methyl-5-phenylfuro[2,3-b]pyridine-3-carbaldehyde (700 mg);

2R*,3S*-2,3-dihydro-2-[(E)-2-buten-2-yl]-4-hydroxy-3-hydroxymethyl-3-methyl-5-phenylfuro[2,3-b]pyridine (8.4 mg);

2R*,3R -2,3-dihydro-2-[(E)-2-buten-2-yl]-4-hydroxy-3-hydroxymethyl-3-methyl-7-phenylfuro[3,2-c]pyridine (18.3 mg);

2R*,4aR*,9aS*-4a,9a-dihydro-5-hydroxy-8-phenyl-2,3,4a-trimethyl-2H-pyrano[2,3-b]furo[3,2-c]pyridine (2.8 mg);

Compound 2 (10.2 mg);

1 R*,4bS*-1,3,4a,4b-tetrahydro-9-hydroxy-4b-methyl-8-phenyl-4-(E)-ethylidenepyrano[4,3-b]furo[2,3-b]pyridine (16.2 mg); and 2,3-dihydro-2-[(E)-2-buten-2-yl] -3,3-di-(hydroxymethyl)-4-hydroxy-5-phenylfuro[2,3-b]pyridine (3.3 mg).

The following two compounds were also isolated from the liquid fermentation broth (3 L) using almost the same purification steps as shown above, but the final HPLC purification was performed with acetonitrile-water (1:4):

2R*,3S*-2,3-dihydro-2,4-dihydroxy-3-[(E)-3-hydroxy-2-methyl-1-butenyl]-7-phenylfuro[3,2-c]pyridine (diastereomer A, 5.6 mg), and a diastereomer of 2R*,3S*-2,3-dihydro-2,4-dihydroxy-3-[(E)-3-hydroxy-2-methyl-1-butenyl]-7-phenylfuro[3,2-c]pyridine (diastereomer B, 7.3 mg).

HPLC Analysis

Analytical HPLC of samples containing the furopyridine compounds were performed using a YMC-pack ODS-AM AM-310-3 column (6.0×50 mm, sold under the tradename of Yamamura) and eluted with acetonitrile-water gradient system: 10:90 (v/v) to 35:65 in first 2 min., 35:65 to 60:40 in subsequent 7.5 min., 60:40 to 100:0 in final 3 min., at a flow rate of 0.9 mL/min. The retention times of the extracted furopyridine compounds were as follows:

2R*,3R*-2,3-dihydro-2-[(E)-2-buten-2-yl]-4-hydroxy-3-methyl-5-phenylfuro[2,3-b]pyridine-3-carbaldehyde (6.4 min.);

2R*,3S*-2,3-dihydro-2-[(E)-2-buten-2-yl]-4-hydroxy-3-hydroxymethyl-3-methyl-5-phenylfuro[2,3-b]pyridine (7.9 min.);

2R*,3R*-2,3-dihydro-2-[(E)-2-buten-2-yl]-4-hydroxy-3-hydroxymethyl-3-methyl-7-phenylfuro[3,2-c]pyridine (7.6 min.);

2R*,4aR*,9aS*-4a,9a-dihydro-5-hydroxy-8-phenyl-2,3,4a-trimethyl-2H-pyrano[2,3-b]furo[3,2-c]pyridine (8.2 min.);

Compound 2 (9.0 min.);

1 R*,4bS*-1,3,4a,4b-tetrahydro-9-hydroxy-4b-methyl-8-phenyl-4-(E)-ethylidenepyrano[4,3-b]furo[2,3-b]pyridine (5.1 min.);

2,3-dihydro-2-[(E)-2-buten-2-yl]-3,3-di-(hydroxymethyl)-4-hydroxy-5-phenylfuro[2,3-b]pyridine (5.8 min.);

2R*,3S*-2,3-dihydro-2,4-dihydroxy-3-[(E)-3-hydroxy-2-methyl-1-butenyl]-7-phenylfuro[3,2-c]pyridine (diastereomer A) (4.4 min.); and 2R*,3S*-2,3-dihydro-2,4-dihydroxy-3-[(E)-3-hydroxy-2-methyl-1-butenyl]-7-phenylfuro[3,2-c]pyridine (diastereomer B) (4.4 min.).

Characterization of the Compounds Isolated From Fermentation Medium

The compounds shown in the above Extraction and Isolation section were characterized for their physico-chemical data. Spectral and physico-chemical data for the furopyridine compounds of this invention were obtained by the following instruments: mp (uncorrected), Yanako Micro Melting Point Apparatus; IR, Shimadzu IR-470; UV, JASCO Ubest-30; Optical rotations, JASCO DIP-370 with a 5 cm cell; NMR, JEOL JNM-GX270 equipped with a LSI-11/73 host computer, TH-5 tunable probe and version 1.6 software; and FAB-MS, JEOL JMS-700. Spectral data for biotransformed products were obtained by the following instruments: UV, Shimadzu UV160U spectrophotometer; NMR, Varian Unity Plus 400 MHz; and FAB-MS, VG Analytical ZAB 2SE high field mass spectrometer. All NMR spectra were measured in acetone-$d_6$ unless otherwise indicated and peak positions are expressed in parts per million (ppm) based on the reference of acetone peak at 2.0 ppm for $^1$H NMR and 30.3 ppm for $^{13}$C NMR. The peak shapes are denoted as follows: s (singlet), d (doublet), t (triplet), q (quartet), m (multiplet) and br (broad). All FAB-MS spectra were measured using glycerol-matrix. The physico-chemical properties and spectral data of these compounds were as follows:

2R*,3R*-2,3-dihydro-2-[(E)-2-buten-2-yl]-4-hydroxy-3-methyl-5-phenylfuro[2,3-b]pyridine-3-carbaldehyde: colorless needle crystals; mp 198~199° C.; molecular formula $C_{19}H_{19}NO_3$; LRFAB-MS m/z 310 [M+H]$^+$; HRFAB-MS m/z 310.1429 (calcd. for $C_{19}H_{20}NO_3$, 310.1444); [α]$_D^{24}$+21.2° (c 0.52, MeOH); UV λ$_{max}$ (MeOH) nm (ε) 209.0 (24,000), 234.0 (19,000); IR ν$_{max}$ (KBr) cm$^{-1}$ 3025, 1724, 1645, 1593, 1440, 1413, 1374, 1289, 1201, 1063, 1049, 1013, 792, 696; $^1$H NMR δ 9.57 (s, 1H), 7.74 (s, 1H), 7.43 (m, 2H), 7.39 (m, 2H), 7.36 (m, 1H), 5.78 (q, J=6.6 Hz, 1H), 4.96 (s, 1H), 1.61 (d, J=6.6 Hz, 3H), 1.60 (s, 3H), 1.53 (s, 3H); $^{13}$C NMR δ 201.15 (d), 131.81 (s), 130.79 (d×2), 129.92 (d×2), 128.77 (d), 125.50 (d), 107.84 (s), 59.17 (s), 20.68 (q), 13.53 (q), 13.52 (q).

2R*,3S*-2,3-dihydro-2-[(E)-2-buten-2-yl]-4-hydroxy-3-hydroxymethyl-3-methyl-5-phenylfuro[2,3-b]pyridine: colorless needle crystals; mp 207~208° C.; molecular formula $C_{19}H_{21}NO_3$; LRFAB-MS m/z 312 [M+H]$^+$; HRFAB-MS m/z 312.1595 (calcd. for $C_{19}H_{22}NO_3$, 312.1601); [α]$_D^{24}$+52.3° (c 0.09, MeOH); UV λ$_{max}$ (MeOH) nm (ε) 208.5 (24,000), 233.0 (19,000); IR ν$_{max}$ (KBr) cm$^{-1}$ 3035, 1594, 1431, 1297, 1235, 1193, 1070, 1050, 945, 791, 698; $^1$H NMR δ 7.78 (s, 1H), 7.49 (m, 2H), 7.33 (m, 2H), 7.23 (m, 1H), 5.59 (q, J=6.8 Hz, 1H), 4.80 (s, 1H), 3.75 (d, J=10.3 Hz, 1H), 3.69 (d, J=10.3 Hz, 1H), 1.58 (d, J=6.8 Hz, 3H), 1.50 (s, 3H), 1.47 (s, 3H); $^{13}$C NMR δ 137.31 (s), 133.71 (s), 130.57 (d×2), 129.29 (d×2), 127.95 (d), 125.29 (d), 111.78 (s), 95.31 (d), 67.22 (t), 50.44 (s), 25.74 (q), 13.53 (q), 13.38 (q).

2R*,3R*-2,3-dihydro-2-[(E)-2-buten-2-yl]-4-hydroxy-3-hydroxymethyl-3-methyl-7-phenylfuro[3,2-c]pyridine: colorless powder; molecular formula $C_{19}H_{21}NO_3$; LRFAB-MS m/z 312 [M+H]$^+$; HRFAB-MS m/z 312.1598 (calcd. for $C_{19}H_{22}NO_3$, 312.1601); [α]$_D^{24}$+15.4° (c 0.26, MeOH); UV λ$_{max}$ (MeOH) nm (ε) 206.5 (22,000), 246.0 (21,000); IR ν$_{max}$ (KBr) cm 3395, 2975, 1647, 1611, 1444, 1213, 1055, 782, 694; $^1$H NMR δ 7.59 (s, 1H), 7.57 (m, 2H), 7.35 (m, 2H), 7.27 (m, 1H), 5.59 (q, J=7.0 Hz, 1H), 5.27 (brs, 1H), 4.90 (s, 1H), 3.66 (s, 2H), 1.67 (s, 3H), 1.65 (d, J=7.0 Hz, 3H), 1.17 (s, 3H); $^{13}$C NMR δ 166.80 (s), 163.27 (s), 135.81 (d), 134.75 (s), 133.10 (s), 129.84 (d×2), 128.91 (d×2), 128.50 (d), 124.29 (d), 117.05 (s), 111.62 (s), 95.15 (d), 70.05 (t), 52.04 (s), 17.54 (q), 14.39 (q), 13.61 (q).

2R*,4aR*,9aS*-4a,9a-dihydro-5-hydroxy-8-phenyl-2,3,4a-trimethyl-2H-pyrano[2,3-b]furo[3,2-c]pyridine: colorless needle crystals; mp 243~244° C.; molecular formula $C_{19}H_{19}NO_3$; LRFAB-MS m/z 310 [M+H]$^+$; HRFAB-MS m/z 310.1456 (calcd. for $C_{19}H_{20}NO_3$, 310.1444); [α]$_{D24}$-22.7° (c 0.33, MeOH); UV λ$_{max}$ (MeOH) (E) nm 207.0 (28,000), 247.0 (27,000); IR ν$_{max}$ (KBr) cm$^{-1}$ 3435, 2940, 1659, 1617, 1428, 1215, 1157, 911, 838, 781, 693; $^1$H NMR δ 10.57 (brs, 1H), 7.55 (m, 2H), 7.48 (s, 1H), 7.35 (m, 2H), 7.25 (m, 1H), 5.90 (s, 1H), 5.71 (s, 1H), 4.35 (q, J=7.6 Hz, 1H), 1.62 (s, 3H), 1.50 (s, 3H), 1.25 (d, J=7.6 Hz, 3H); 13C NMR δ 164.61 (s), 161.28 (s), 135.87 (d), 135.61 (s), 134.80 (s), 129.79 (d×2), 128.84 (d×2), 128.31 (d), 124.67 (d), 116.80 (s), 112.79 (d), 110.50 (s), 68.14 (d), 43.00 (s), 23.68 (q), 19.89 (q), 19.50 (q).

1R*,4bS*-1,3,4a,4b-tetrahydro-9-hydroxy-4b-methyl-8-phenyl-4-(E)-ethylidenepyrano[4,3-b]furo[2,3-b]pyridine: colorless needle crystals; mp 234~235° C.; molecular formula $C_{19}H_{19}NO_4$; LRFAB-MS m/z 326 [M+H]$^+$; HRFAB-MS m/z 326.1398 (calcd. for $C_{19}H_{20}NO_4$, 326.1393); $[\alpha]_D^{24}$+205.0° (c 0.12, MeOH); UV $\lambda_{max}$ (MeOH) nm (F) 208.5 (28,000), 235.0 (25,000); IR $\nu_{max}$ (KBr) cm$^{-1}$ 3055, 1645, 1597, 1441, 1414, 1376, 1198, 1078, 947, 794, 697; $^1$H NMR δ 7.66 (s, 1H), 7.51 (m, 2H), 7.31 (m, 2H), 7.24 (m, 1H), 5.86 (q, J=7.0 Hz, 1H), 4.81 (s, 1H), 4.75 (s, 1H), 4.44 (s, 2H), 1.61 (d, J=7.0 Hz, 3H), 1.41 (s, 3H); $^{13}$C NMR δ 144.23 (d), 137.34 (s), 132.24 (s), 130.47 (d×2), 129.19 (d×2), 127.94 (d), 124.54 (d), 100.39 (d), 92.29 (d), 64.11 (t), 53.21 (s), 22.25 (q), 13.53 (q).

2,3-dihydro-2-[(E)-2-buten-2-yl]-3,3-di-(hydroxymethyl)-4-hydroxy-5-phenylfuro[2,3-b]pyridine: colorless needle crystals; mp 214~216° C.; molecular formula $C_{19}H_{21}NO_4$; LRFAB-MS m/z 328 [M+H]$^+$; HRFAB-MS m/z 328.1534 (calcd. for $C_{19}H_{22}NO_4$, 328.1549); $[\alpha]_D^{24}$+40.0° (c 0.02, MeOH); UV $\lambda_{max}$ (MeOH) run (E) 207.5 (15,000), 234.5 (13,000); IR $\nu_{max}$ (KBr) cm$^{-1}$ 3073, 1643, 1597, 1436, 1379, 1156, 1070, 944, 796, 697; $^1$H NMR δ 7.73 (s, 1H), 7.49 (d, J=7.0 Hz, 2H), 7.31 (t, J=7.0 Hz, 2H), 7.23 (t, J=7.0 Hz, 1H), 5.54 (q, J=7.0 Hz, 1H), 5.05 (s, 1H), 3.98 (d, J=7.3 Hz, 1H), 3.94 (d, J=7.3 Hz, 1H), 3.59 (d, J=7.3 Hz, 1H), 3.51 (d, J=7.3 Hz, 1H), 1.58 (d, J=7.0 Hz, 3H), 1.53 (s, 3H); 13C NMR δ 162.61 (s), 148.90 (d), 137.80 (s), 133.93 (s), 130.54 (d×2), 129.20 (d×2), 127.72 (d), 124.38 (d), 90.15 (d), 63.94 (t), 61.98 (t), 56.30 (s), 13.61 (q), 13.51 (q).

2R*,3S*-2,3-dihydro-2,4-dihydroxy-3-[(E)-3-hydroxy-2-methyl-1-butenyl]-7-phenylfuro[3,2-c]pyridine (diastereomer A): colorless powder; molecular formula $C_{19}H_{21}NO_4$; LRFAB-MS m/z 328 [M+H]$^+$; HRFAB-MS m/z 328.1559 (calcd. for $C_{19}H_{22}NO_4$, 328.1550); $[\alpha]_D^{24}$+7.40° (c 0.11, MeOH); UV $\lambda_{max}$ (MeOH) nm (E) 206.5 (23,000), 245.0 (23,000); IR $\nu_{max}$ (KBr) cm$^{-1}$ 3375, 1648, 1614, 1428, 1311, 1154; $^1$H NMR δ 7.55 (m, 2H), 7.51 (s, 1H), 7.33 (m, 2H), 7.24 (m, 1H), 5.98 (s, 1H), 5.77 (s, 1H), 4.08 (q, J=6.8 Hz, 1H), 1.62 (s, 3H), 1.50 (s, 3H), 1.12 (d, J=6.8 Hz, 3H); $^{13}$C NMR δ 164.29 (s), 161.69 (s), 143.27 (s), 135.61 (d), 135.16 (s), 129.72 (d×2), 128.90 (d×3), 128.27 (d), 117.25 (s), 111.23 (d), 110.80 (s), 74.19 (d), 49.78 (s), 22.86 (q), 22.86 (q), 12.98 (q).

2R*,3S*-2,3-dihydro-2,4-dihydroxy-3-[(E)-3-hydroxy-2-methyl-1-butenyl]-7-phenylfuro[3,2-c]pyridine (diastereomer B): colorless powder; molecular formula $C_{19}H_{21}NO_4$; LRFAB-MS m/z 328 [M+H]$^+$; HRFAB-MS m/z 128.1570 (calcd. for $C_{19}H_{22}NO_4$, 328.1550); $[\alpha]_D^{24}$+2.17° (c 0.14, MeOH); UV $\lambda_{max}$ (MeOH) nm (F) 207.0 (22,000), 245.5 (22,000); IR $\nu_{max}$ (KBr) cm$^{-1}$ 3384, 1649, 1609, 1427, 1152, 1047, 874, 694; $^1$H NMR δ 7.55 (m, 2H), 7.54 (s, 1H), 7.33 (m, 2H), 7.24 (m, 1H), 5.99 (s, 1H), 5.74 (s, 1H), 4.08 (q, J=6.8 Hz, 1H), 1.62 (s, 3H), 1.49 (s, 3H), 1.12 (d, J=6.8 Hz, 3H); $^{13}$C NMR δ 164.42 (s), 161.83 (s), 143.31 (s), 135.68 (d), 135.15 (s), 129.72 (d×2), 128.91 (d×3), 128.28 (d), 117.40 (s), 111.48 (s), 110.92 (s), 74.26 (d), 49.70 (s), 22.81 (q), 22.81 (q), 12.94 (q).

Compound 2: colorless powder; molecular formula $C_{19}H_{19}NO_2$; LRFAB-MS m/z 292 [M-H]-; HRFAB-MS m/z 292.1319 (calcd. for $C_{19}H_{19}NO_2$, 292.1338); $[\alpha]_D^{24}$+13.3° (c 0.06, MeOH); UV $\lambda_{max}$ (MeOH) nm (6) 206.0 (21,000), 247.0 (22,000); IR $\nu_{max}$ (KBr) cm$^{-1}$ 3378, 2963, 1647, 1614, 1450, 1427, 1228, 1042, 823, 774, 694; $^1$H NMR δ 7.52 (m, 2H), 7.47 (s, 1H), 7.31 (m, 2H), 7.24 (m, 1H), 5.36 (brs, 1H), 3.13 (brs, 1H), 2.78 (q, J=7.3 Hz, 1H), 1.67 (s, 3H), 1.58 (s, 3H), 1.18 (d, J=7.3 Hz, 3H); $^{13}$C NMR δ 165.03 (s), 162.55 (s), 151.38 (s), 135.38 (d), 130.23 (s), 129.71 (d×2), 128.79 (d×2), 128.15 (d), 127.81 (d), 114.34 (s), 111.06 (s), 104.28 (s), 58.32 (d), 50.30 (d), 26.97 (q), 20.93 (q), 15.28 (q).

Example 2

Biotransformation of Compound 1 (2R*,3R*-2,3-dihydro-2-[(E)-2-buten-2-yl]-4-hydroxy-3-methyl-5-phenylfuro[2,3-b]pyridine-3-carbaldehyde)

Microorganisms

Cultures of *Calonectria decora* (FERM BP-6124), *Cunninghamella echinulata* var. *elegans* (FERM BP-6126), and an unidentified bacterium (FERM BP-6125) were maintained as spore suspensions (FERM BP-6124 and FERM BP-6126) or vegetative mycelium (FERM BP-6125) in 13.3% glycerol frozen at −80° C.

Biotransformation Conditions

Biotransformation screening experiments were carried out in the medium described by R. V. Smith and J. P. Rosazza (*J Pharm. Sci.*, 64, 1737–1759, 1975) which contains glucose (20 g), NaCl (5 g), $K_2HPO_4$ (5 g), yeast extract (5 g), and soy flour (5 g) in 1 L of deionized water. The mixture was adjusted to pH 7.0 and autoclaved at 121° C. for 20 min. Screening was conducted in 16×125 mm test tubes containing 2.5 mL of medium which was inoculated with 0.05 mL of frozen glycerol stock. One day after inoculation, 0.05 mL of a 5 mg/mL solution of 2R*,3R*-2,3-dihydro-2-[(E)-2-buten-2-yl]-4-hydroxy-3-methyl-5-phenylfuro[2,3-b]pyridine-3-carbaldehyde in dimethysulfoxide (DMSO) was added, giving a final broth concentration of 0.1 mg/rnL. Tubes were incubated with shaking at 220 rpm at 28° C. for 1 to 6 days.

For isolation of the bioconversion products, cultures FERM BP-6124 and FERM BP-6126 were scaled up into 125 mL Erlenmeyer or 2800 mL Fernbach flasks. The Erlenmeyer flasks contained 25 mL and the Fembach flasks 250 mL of the described medium. Each was inoculated with a 10 percent preformed inoculum stage grown 2–3 days in the same medium. For culture FERM BP-6125, the inoculum and biotransformation media described by T. S. Chen et al. (*J. Antibiotics*, 45, 577–580, 1992) were used in the same proportions. 2R*,3R*-2,3-dihydro-2-[(E)-2-buten-2-yl]-4-hydroxy-3-methyl-5-phenylfuro[2,3-b]pyridine-3-carbaldehyde was added to a final concentration of 0.1 mg/mL medium one day after inoculation and incubation continued 3 days.

Assay

2R*,3R*-2,3-dihydro-2-[(E)-2-buten-2-yl]-4-hydroxy-3-methyl-5-phenylfuro[2,3-b]pyridine-3-carbaldehyde and its biotransformation products were detected by HPLC on a Waters Millennium system comprised of a 600 controller, 717 autosampler and a 996 photodiode array detector. Broth samples (2.5 ml) were adjusted to pH 6 if necessary then extracted with an equal volume of ethyl acetate. The organic layer was removed and evaporated to dryness with nitrogen, after which the solids were reconstituted in 1 mL of methanol. Samples (20 PL) were run on a 5 $\mu$ Inertsil C8 column (4.6×250 mm) and eluted with 20 mM $KH_2PO_4$ pH 6: acetonitrile (67:33) at a flow rate of 1 mL/mL and a run time of 30 min. Eluate was monitored by UV absorbance at 233 nm.

Isolation of Biotransformation Products

Broths (total volumes: 1.6 L to 4.2 L) from the bioconversion fermentations were extracted three times with an equal volume of ethyl acetate. When analyzed by HPLC, no significant residual products remained in the broth. The extract was brought to dryness by rotary evaporation under reduced pressure, and the dried extract was washed with 10 mL of hexane. The hexane fraction was decanted and an aliquot dried and reconstituted in methanol for HPLC analysis. No significant amounts of desired products were detected in the hexane fraction. The remaining dried extract pellet was dissolved in 1.0 mL DMSO. Partial purification of this material was achieved by elution from a 10 g YMC-XQSFAQ 100 solid phase extraction cartridge with a stepwise gradient of acetonitrile and water. Fractions containing the materials of interest were first stripped of solvent and then reextracted three times with ethyl acetate and subjected to further purification by HPLC using the system described above with the following modifications: 20×250 mm semi-preparative 5 ti Inertsil C8 column with a 50×20 mm 10 μ C8 Inertsil guard column and a modified mobile phase with a 78:22 ratio of 20 mM $KH_2PO_4$ pH 6: acetonitrile. Fractions corresponding to the peaks of interest were pooled, stripped of solvent, extracted with ethyl acetate, and dried to yield the final products. From 4.2 L of FERM BP-6124 culture, 77.2 mg of 2R*,3R*-2,3-dihydro-4-hydroxy-2-[(E)-4-hydroxy-2-buten-2-yl]-3-methyl-5-phenylfuro[2,3-b]pyridine-3-carbaldehyde was isolated. From 3.2 L of FERM BP-6126 culture, 8.1 mg of 2R*,3R*-2,3-dihydro-2-[(E)-2-buten-2-yl]-4-hydroxy-5-(4-hydroxyphenyl)-3-methylfuro[2,3-b]pyridine-3-carbaldehyde was isolated, and from 1.6 L of FERM BP-6126 culture, 35.4 mg of 2R*,3S*-2,3-dihydro-4-hydroxy-2-[(E)-4-hydroxy-2-buten-2-yl]-3-hydroxymethyl-3-methyl-5-phenylfuro[2,3-b]pyridine was isolated.

Characterization of Biotransformed Compounds

Spectral and physico-chemical data for the biotransformed compounds were obtained as described above. The physico-chemical properties and spectral data of these compounds were as follows.

2R*,3R*-2,3-dihydro-4-hydroxy-2-[(E)-4-hydroxy-2-buten-2-yl]-3-methyl-5-phenylfuro[2,3-b]pyridine-3-carbaldehyde: colorless powder; molecular formula $C_{19}H_{19}NO_4$; LRFAB-MS m/z 326 [M+H]$^+$; HRFAB-MS m/z 326.1376 (calcd. for $C_{19}H_{20}NO_4$, 326.1392); UV $\lambda_{max}$ (EtOH) nm (E) 208.0 (33,400), 233.0 (24, 200); $^1$H NMR δ 9.55 (s, 1H), 7.62 (s, 1H), 7.50 (d, J=7.5 Hz, 2H), 7.32 (t, J=7.5 Hz, 2H), 7.22 (t, J=7.5 Hz, 1H), 5.86 (t, J=6 Hz, 1H), 4.88 (s, 1H), 4.14 (d, J=6 Hz, 2H), 1.61 (s, 3H), 1.57 (s, 3H).

2R*,3R*-2,3-dihydro-2-[(E)-2-buten-2-yl]-4-hydroxy-5-(4-hydroxyphenyl)-3-methylfuro[2,3-b]pyridine-3-carbaldehyde: colorless powder; molecular formula $C_{19}H_{19}NO_4$; LRFAB-MS m/z 326 [M+H]$^+$; HRFAB-MS m/z 326.1380 (calcd. for $C_{19}H_{20}NO_4$, 326.1392); UV $\lambda_{max}$ (EtOH) nm (ε) 211.0 (17,200), 245.0 (11, 800); $^1$H NMR δ 9.57 (s, 1H), 7.65 (s, 1H), 7.27 (d, J=8.5 Hz, 2H), 6.83 (t, J=8.5 Hz, 2H), 5.77 (q, J=6.6 Hz, 1H), 4.90 (s, 1H), 1.62 (d, J=6.6 Hz, 3H), 1.59 (s, 3H), 1.55 (s, 3H).

2R*,3S*-2,3-dihydro-4-hydroxy-2-[(E)-4-hydroxy-2-buten-2-yl]-3-hydroxymethyl-3-methyl-5-phenylfuro[2,3-b]pyridine: colorless powder; molecular formula $C_{19}H_{21}NO_4$; LRFAB-MS m/z 328 [M+H]$^+$; HRFAB-MS m/z 328.1534 (calcd. for $C_{19}H_{22}NO_4$, 328.1549); UV $\lambda_{max}$ (EtOH) nm (E) 211.0 (52,000), 234.0 (45, 300); $^1$H NMR δ 7.82 (s, 1H), 7.53 (d, J=7.5 Hz, 2H), 7.38 (t, J=7.5 Hz, 2H), 7.28 (t, J=7.5 Hz, 1H), 5.72 (t, J=6 Hz, 1H), 4.86 (s, 1H), 4.14 (d, J=6 Hz, 2H), 3.80 (s, 2H), 1.58 (s, 3H), 1.53 (s, 3H).

The chemical structures of the compounds prepared in the working examples are summarized in the following Table.

TABLE

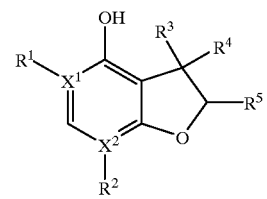

(I)

| Exam. No. | $X^1$ | $X^2$ | $R^1$ | $R^2$ | $R^3$ | $R^4$ | $R^5$ |
|---|---|---|---|---|---|---|---|
| 1 | C | N | Ph. | — | $CH_3$ | formyl | a) |
| 1 | C | N | Ph | — | $CH_3$ | b) | a) |
| 1 | C | N | Ph. | — | $CH_3$ | c) | |
| 1 | C | N | Ph. | — | b) | b) | a) |
| 1 | N | C | — | Ph. | $CH_3$ | b) | a) |
| 1 | N | C | — | Ph. | $CH_3$ | d) | |
| 1 | N | C | — | Ph. | $CH_3$ | e) | OH |
| 2 | C | N | Ph. | — | $CH_3$ | formyl | g) |
| 2 | C | N | f) | — | $CH_3$ | formyl | a) |
| 2 | C | N | Ph. | — | $CH_3$ | b) | g) |

Ph: phenyl
a): 2-buten-2-yl;
b): hydroxymethyl
c):

d):

e): 3-hydroxy-2-methyl-1-buten-1-yl;
f): p-hydroxyphenyl;
g): 4-hydroxy-2-buten-2-yl.

Assay

The compound prepared in Example 1(2R*,3R*-2,3-dihydro-2-[(E)-2-buten-2-yl]-4-hydroxy-3-methyl-5-phenylfuro[2,3-b]pyridine-3-carbaldehyde ) was tested according to the assay method described in pages 12 to 14. The results of the assay are summarized in the following table.

TABLE

| Compound | Example 1 |
|---|---|
| Staphylococcus aureus 01A1095 | 100 |
| S. aureus 01A1105 | 25 (19 mm) |
| S. aureus 01A1120 | 25 |
| S. hemolyticus 01E1006 | 100 |
| Streptococcus agalactiae 02B1023 | 25 |
| S. pyogenes 02C1068 | 6.25 (13 mm) |
| S. pyogenes 02C1079 | 12.5 |
| S. pneumoniae 02J1046 | 25 |

TABLE-continued

| Compound | Example 1 |
|---|---|
| S. pneumoniae 02J1095 | 6.25 |
| Enterococcus faecalis 03A1069 | 100 (10 mm) |
| Haemophilus influenzae 54A0085 | 50 |
| H. influenzae 54A0131 | 100 |
| Moraxella catarrhalis 87A1055 | 50 |
| Escherichia coli 51A0266 | >100 (0 mm) |
| E. coli 51A1051 | >100 |
| E. coli 51A1073 | >100 |
| E. coli 51A1074 | >100 |
| E. coli 51A1075 | 100 |

*Zone size; compound: 100 mg/disc, control compound: 10 mg/disc.

As shown in the above table, it was confirmed that the compound of Example 1(2R*-3R*-2,3-dihydro-2-[(E)-2-buten-2-yl]-4-hydroxy-3-methyl-5-phenylfuro[2,3-b]pyridine-3-carbaldehyde) has remarkable antibacterial activity against various bacteria.

What is claimed is:

1. A compound having the structure:

wherein $X^1$ is C, $X^2$ is N, $R^1$ is phenyl, $R^2$ is absent, $R^3$ is methyl, $R^4$ and $R^5$ together form the following:

$X^1$ is C, $X^2$ is N, $R^1$ is phenyl, $R^2$ is absent, $R^3$ and $R^4$ are hydroxymethyl, and $R^5$ is 2-buten-2-yl;

$X^1$ is C, $X^2$ is N, $R^1$ is phenyl, $R^2$ is absent, $R^3$ is methyl, $R^4$ is formyl, and $R^5$ is 4-hydroxy-2-buten-2-yl;

$X^1$ is C, $X^2$ is N, $R^1$ is phenyl, $R^2$ is absent, $R^3$ is methyl, $R^4$ is hydroxymethyl, and $R^5$ is 4-hydroxy-2-buten-2-yl;

$X^1$ is N; $X^2$ is C; $R^1$ is absent; $R^2$ is phenyl; $R^3$ is methyl; $R^4$ is hydroxymethyl; and $R^5$ is 2-buten-2-yl;

$X^1$ is N; $X^2$ is C; $R^1$ is absent; $R^2$ is phenyl; $R^3$ is methyl; $R^4$ and $R^5$, together with the carbon atoms to which they are attached, form the following ring:

or $X^1$ is N; $X^2$ is C; $R^1$ is absent; $R^2$ is phenyl; $R^3$ is methyl; $R^4$ is 3-hydroxy-2-methyl-1-buten-1-yl; and $R^5$ is OH;

or a pharmaceutically acceptable salt thereof.

2. A compound according to claim 1, selected from
2R*,3R*-2,3-dihydro-2-[(E)-2-buten-2-yl]-4-hydroxy-3-hydroxymethyl-3-methyl-7-phenylfuro[3,2-c]pyridine;
2R*,4aR*,9aS*-4a,9a-dihydro-5-hydroxy-8-phenyl-2,3,4a-trimethyl-2H-pyrano[2,3-b]furo[3,2-c]pyridine;
1R*,4bS*-1,3,4a,4b-tetrahydro-9-hydroxy-4b-methyl-8-phenyl-4-(E)-ethylidenepyrano[4,3-b]furo[2,3-b]pyridine;
2,3-dihydro-2-[(E)-2-buten-2-yl]-3,3-di-(hydroxymethyl)-4-hydroxy-5-phenylfuro[2,3-b]pyridine;
2R*,3S*-2,3-dihydro-2,4-dihydroxy-3-[(E)-3-hydroxy-2-methyl-1-butenyl]-7-phenylfuro[3,2-c]pyridine;
2R*,3R*-2,3-dihydro-4-hydroxy-2-[(E)-4-hydroxy-2-buten-2-yl]-3-methyl-5-phenylfuro[2,3-b]pyridine-3-carbaldehyde; and
2R*,3S*-2,3-dihydro-4-hydroxy-2-[(E)-4-hydroxy-2-buten-2-yl]-3-hydroxymethyl-3-methyl-5-phenylfuro[2,3-b]pyridine; and the pharmaceutically acceptable salts thereof.

3. A pharmaceutical composition for use in the treatment of infectious diseases caused by bacteria, which comprises a compound according to claim 1 or a pharmaceutically acceptable salt thereof in an amount effective in such treatments; and a pharmaceutically acceptable carrier.

4. A method of treating infectious diseases caused by bacteria, in a mammalian subject, which comprises administering to said subject a therapeutically effective amount of a compound according to claim 1.

* * * * *